United States Patent [19]

Furutaka et al.

[11] Patent Number: 5,132,473

[45] Date of Patent: Jul. 21, 1992

[54] PROCESS FOR PRODUCTION OF 1,1,1-TRIFLUORO-2,2-DICHLOROETHANE

[75] Inventors: Yasuhisa Furutaka, Takatsuki; Yukio Homoto, Katano; Tsunetoshi Honda, Settsu, all of Japan

[73] Assignee: Daikin Industries, Ltd., Osaka, Japan

[21] Appl. No.: 586,373

[22] Filed: Sep. 21, 1990

Related U.S. Application Data

[63] Continuation of Ser. No. 349,177, May 9, 1989, abandoned.

[30] Foreign Application Priority Data

May 17, 1988 [JP] Japan .................. 63-120068

[51] Int. Cl.$^5$ .................. C07C 17/158; C07C 19/02
[52] U.S. Cl. .................. 570/123
[58] Field of Search .................. 570/123, 245

[56] References Cited

U.S. PATENT DOCUMENTS

| | | | |
|---|---|---|---|
| 2,636,864 | 4/1953 | Pye et al. | 570/245 |
| 2,644,845 | 7/1953 | McBee | 570/174 |
| 2,846,484 | 8/1958 | Fox | 570/245 |
| 2,952,714 | 9/1960 | Milam et al. | 570/245 |
| 3,042,728 | 7/1962 | Hirsh et al. | 570/245 |
| 3,755,477 | 8/1973 | Firth et al. | 260/653.4 |
| 4,060,469 | 11/1977 | Sweeney | 204/163 R |
| 4,145,368 | 3/1979 | Sweeney et al. | 570/163 |

FOREIGN PATENT DOCUMENTS

| | | |
|---|---|---|
| 53-82711 | 7/1978 | Japan . |
| 58-222038 | 12/1983 | Japan . |
| 61-27375 | 6/1986 | Japan . |

OTHER PUBLICATIONS

E. T. McBee et al, "Fluorinated Derivatives of Ethane", Industrial and Engineering Chemistry, Mar., 1947, pp. 409–412, vol. 39, No. 3.

*Primary Examiner*—J. E. Evans
*Attorney, Agent, or Firm*—Birch, Stewart, Kolasch & Birch

[57] ABSTRACT

A process for production of 1,1,1-trifluoro-2,2-dichloroethane comprising reacting 1,1,1-trifluoro-2-chloroethane with hydrogen chloride and oxygen in the presence of a metal salt as a catalyst.

5 Claims, No Drawings

PROCESS FOR PRODUCTION OF 1,1,1-TRIFLUORO-2,2-DICHLOROETHANE

This application is a continuation of application Ser. No. 349,177, filed on May 9, 1989, now abandoned.

BACKGROUND OF THE INVENTION

1. Field of the Invention

The present invention relates to a process for the production of 1,1,1-trifluoro-2,2-dichloroethane. Particularly, the present invention relates to a process for the production of 1,1,1-trifluoro-2,2-dichloroethane comprising reacting 1,1,1-trifluoro-2-chloroethane with hydrogen chloride and oxygen in the presence of a metal salt as a catalyst.

2. Description of the Related Art 1,1,1-Trifluoro-2,2-dichloroethane is expected to replace trichlorofluoromethane, since it does not decompose ozone in the stratosphere. Thus, it is desirable to develop an economical process for the production of 1,1,1-trifluoro-2,2-dichloroethane.

Several processes for the production of 1,1,1-trifluoro-2,2-dichloroethane have been already proposed. For example, Czechoslovakian Patent No. 136,735 and Japanese Patent Kokai Publication No. 222038/1983 describe a process comprising reduction of 1,1,1-trifluoro-2,2,2-trichloroethane. Japanese Patent Publication No. 27375/1986 describes a process comprising isomerization of 1,1,2-trifluoro-1,2-dichloroethane. U.S. Patent No. 3,755,477 describes a process comprising fluorination of ethylene tetrachloride. Japanese Patent Kokai Publication No. 82711/1978 describes a process comprising photo chlorination of 1,1,1-trifluoro-2-chloroethane.

However, from a point of view of the economical production, the above known processes for the production of 1,1,1-trifluoro-2,2-dichloroethane are not necessarily suitable since the yield and selectivity through such the processes are not sufficiently high.

SUMMARY OF THE INVENTION

It is, therefore, an object of the present invention to provide a commercially advantageous process for the production of 1,1,1-trifluoro-2,2-dichloroethane in which the problems described above are overcome.

According to the present invention, there is provided a process for the production of 1,1,1-trifluoro-2,2-dichloroethane which process comprises reacting 1,1,1-trifluoro-2-chloroethane with hydrogen chloride and oxygen in the presence of a metal salt as a catalyst.

In the process of the present invention, it is possible to produce 1,1,1-trifluoro-2,2-dichloroethane economically and commercially.

DETAILED DESCRIPTION OF THE INVENTION 1,1,1-Trifluoro-2-chloroethane, as a starting material of the present process, can be easily produced by fluorination of trichloroethylene with anhydrous hydrogen fluoride in a liquid or gas phase.

The metal salt used as the catalyst in the present process includes a metal halide, for example $NiCl_2$, $CuCl_2$, $FeCl_2$ and so on. Also, combination of such the metal halide with KCl provides good results.

It is preferred to use a metal salt which is carried on, for example, a support made of a metal oxide such as aluminum oxide or a metal fluoride such as aluminum fluoride.

The amount of the catalyst carried on the support is suitably selected depending on the reaction conditions, the desired conversion and so on. Generally, the molar ratio of the metal salt as the catalyst to the metal oxide as the support, is in the range of from 0.005 to 2, particularly from 0.01 to 1.0, for example 0.01.

In the process of the present invention, it is most preferable to use $CuCl_2$ supported on the support made of aluminum fluoride.

Generally, a support of size can be used, and it is most preferable to use a spherical support or a pellet form support of a size within the range of from 1 to 10 mm, particularly from 2 to 4 mm.

The amount of 1,1,1-trifluoro-2-chloroethane, hydrogen chloride and oxygen to be supplied to a reactor is preferably controlled so that the amount of hydrogen chloride is more than 0.1 mole, for example 0.5 mole and the amount of oxygen is from 0.05 to 0.5 mole, for example 0.2 mole per mole of 1,1,1-trifluoro-2-chloroethane, respectively. In addition, the reaction is preferably carried out at the molar ratio of oxygen to hydrogen chloride of less than 1, for example at 0.5.

The purity of oxygen is not necessarily 100%, and the oxygen diluted with an inert gas such as nitrogen can be also used in the present process. Commercially, it is advantage to use air from the point of economical view.

The reaction temperature is preferably in the range of from 250° to 550° C., particularly from 350° to 500° C. The present process is generally performed under the atmospheric pressure, although it can be performed under applied pressure. Further, it is also possible to carry out the reaction under dilution by an inert gas such as nitrogen.

The contact time between the catalyst and the reactants can be suitably selected depending on the reaction conditions, especially the reaction temperature. Generally, the contact time is preferably controlled in the range of from 0.5 to 30 seconds.

In the present process, any type of reactor, for example a tube reactor, can be used as long as good contact between the catalyst carried on the catalyst and the reactants is achieved.

In the process of the present invention, the reactor such as the tube-reactor filled with a catalyst is heated to a preselected temperature dependent on the reaction temperature, for example, in an electrical furnace. Then, the reactants (1,1,1-trifluoro-2-chloroethane, hydrogen chloride and oxygen) are supplied to the reactor to initiate the reaction. The exit gas from the reactor is generally collected after water washing and drying steps.

In order to improve the conversion of 1,1,1-trifluoro-2-chloroethane, it is advantageous to recycle the unreacted 1,1,1-trifluoro-2-chloroethane to the reactor which is recovered from the top of a purification apparatus for purifying the produced gas.

The present invention will be hereinafter explained further in detail by following examples.

EXAMPLE 1

A tube reactor made of Hastelloy C (20 mm in inner diameter, 400 mm in length) was filled with 50 ml of spherical support particles (from 2 to 4 mm in diameter) made of $AlF_3$ carrying $NiCl_2$ in the molar ratio of 0.01 to $AlF_3$ and heated to 500° C. in a nitrogen stream. After stopping the supply of nitrogen, 1,1,1-trifluoro-2- chloroethane, hydrogen chloride and oxygen are supplied to the reactor at the flow rate of 100 ml/min., 50 ml/min. and 25 ml/min (based on the standard condition), respectively. The contact time based on the average residence time was about 6 seconds.

The exit gas from the tube reactor was collected after water washing and drying steps, and then analyzed with a gas chromatography. The conversion of 1,1,1-trifluoro-2-chloroethane was 48% and the selectivity to 1,1,1-trifluoro-2,2-dichloroethane was 69%.

EXAMPLES 2 AND 3

Example 1 was repeated except that the support made of $AlF_3$ carrying $CuCl_2$ in the molar ratio of 0.03 to $AlF_3$ was used as the catalyst and the reaction temperature was changed as shown in Table 1.

The results are also shown in Table 1.

TABLE 1

|  | Example 2 | Example 3 |
| --- | --- | --- |
| Reaction temp. | 400° C. | 450° C. |
| Conversion of 1,1,1-trifluoro-2-chloroethane | 35% | 43% |
| Selectivity to 1,1,1-trifluoro-2,2-dichloroethane | 79% | 72% |

EXAMPLES 4-6

Example 2 was repeated except that the flow rates of the reactants supplied to the tube reactor were changed as shown in Table 2.

The results are also shown in Table 2.

TABLE 2

|  | Example 4 | Example 5 | Example 6 |
| --- | --- | --- | --- |
| Flow rate of 1,1,1-trifluoro-2-chloroethane | 100 ml/min. | 100 ml/min. | 100 ml/min. |
| Flow rate of hydrogen chloride | 25 ml/min. | 25 ml/min. | 100 ml/min. |
| Flow rate of oxygen | 5 ml/min. | 25 ml/min. | 25 ml/min. |
| Contact time | 9.4 sec. | 8.1 sec. | 5.4 sec. |
| Conversion of 1,1,1-trifluoro-2-chloroethane | 8% | 22% | 42% |
| Selectivity to 1,1,1-trifluoro-2,2-dichloroethane | 89% | 82% | 73% |

What is claimed is:

1. A process for production of 1,1,1-trifluoro-2,2-dichloroethane comprising reacting 1,1,1-trifluoro-2-chloroethane with hydrogen chloride and oxygen in the presence of a metal salt as a catalyst carried in a support, in which the metal salt is $CuCl_2$ and the support is aluminum fluoride.

2. A process for production of 1,1,1-trifluoro-2,2-dichloroethane comprising reacting 1,1,1-trifluoro-2-chloroethane with hydrogen chloride and oxygen in the presence of a metal salt as a catalyst on a support, in which the support is a metal fluoride.

3. The process according to claim 2, wherein the metal salt is $NiCl_2$, $CuCl_2$ or $FeCl_2$.

4. The process according to claim 2, wherein the support is aluminum fluoride.

5. The process according to claim 4, wherein the metal salt is $NiCl_2$, $CuCl_2$ or $FECl_2$.

* * * * *